(12) United States Patent
Miyamoto (10) Patent No.: US 9,922,409 B2
(45) Date of Patent: Mar. 20, 2018

(54) EDGE EMPHASIS IN PROCESSING IMAGES BASED ON RADIATION IMAGES

(71) Applicant: CANON KABUSHIKI KAISHA, Tokyo (JP)

(72) Inventor: Hideaki Miyamoto, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/986,981

(22) Filed: Jan. 4, 2016

(65) Prior Publication Data

US 2016/0117809 A1   Apr. 28, 2016

Related U.S. Application Data

(63) Continuation of application No. 14/058,554, filed on Oct. 21, 2013, now Pat. No. 9,275,439.

(30) Foreign Application Priority Data

Nov. 7, 2012   (JP) ................................. 2012-245636

(51) Int. Cl.
*G06T 7/13*      (2017.01)
*G06T 5/50*      (2006.01)
(Continued)

(52) U.S. Cl.
CPC ............... *G06T 5/50* (2013.01); *A61B 6/481* (2013.01); *G06T 5/003* (2013.01); *G06T 5/004* (2013.01); *G06T 7/0012* (2013.01); *G06T 7/13* (2017.01); *G06T 11/003* (2013.01); *G06T 2207/10116* (2013.01); *G06T 2207/20192* (2013.01); *G06T 2207/20221* (2013.01); *G06T 2207/20224* (2013.01); *G06T 2207/30101* (2013.01)

(58) Field of Classification Search
CPC ... G06T 7/13; G06T 7/12; G06T 2207/20224; G06T 3/40; H04N 9/646; G06K 9/4604
See application file for complete search history.

(56) References Cited

U.S. PATENT DOCUMENTS 4,672,651 A    6/1987  Horiba et al. ................... 378/62
5,402,338 A  * 3/1995  Ito ........................... G06T 5/004
                                                        250/583

(Continued)

FOREIGN PATENT DOCUMENTS

CN    103295190 A  *  9/2013  ............. G06T 5/002
JP    S62-287374       12/1987
(Continued)

*Primary Examiner* — Iman K Kholdebarin
*Assistant Examiner* — Mai Tran
(74) *Attorney, Agent, or Firm* — Fitzpatrick Cella Harper and Scinto (57) ABSTRACT

A subtraction image is generated by performing subtraction between a mask image serving as a radiation image obtained by capturing an object, at least of a specific region of which does not include contrast medium, and a live image serving as a radiation image obtained by capturing the object which includes the contrast medium. The emphasis degree serving as the degree of emphasis processing for the subtraction image is determined based on at least either the mask image or live image. The emphasis processing is performed for the subtraction image based on the emphasis degree.

16 Claims, 7 Drawing Sheets

(51) Int. Cl.
*G06T 5/00* (2006.01)
*A61B 6/00* (2006.01)
*G06T 7/00* (2017.01)
*G06T 11/00* (2006.01)

(56) References Cited

U.S. PATENT DOCUMENTS

| | | | | |
|---|---|---|---|---|
| 5,600,731 | A | 2/1997 | Sezan | 348/620 |
| 5,633,509 | A * | 5/1997 | Takeo | G01N 23/04 250/583 |
| 5,739,922 | A | 4/1998 | Matama | 358/447 |
| 5,806,521 | A | 9/1998 | Morimoto et al. | 600/447 |
| 5,937,111 | A * | 8/1999 | Yamada | G06T 5/004 382/132 |
| 5,982,953 | A * | 11/1999 | Yanagita | G06F 19/321 348/580 |
| 6,014,474 | A | 1/2000 | Takeo et al. | 382/308 |
| 6,016,356 | A * | 1/2000 | Ito | G06T 5/004 382/132 |
| 6,075,877 | A * | 6/2000 | Takeo | G06T 5/004 378/98.12 |
| 8,299,413 | B2 | 10/2012 | Vogt et al. | 250/208.1 |
| 8,542,794 | B2 * | 9/2013 | Miyamoto | A61B 6/00 250/354.1 |
| 2002/0090052 | A1 * | 7/2002 | Muller | A61B 6/481 378/37 |
| 2003/0218776 | A1 | 11/2003 | Morimoto et al. | 358/2.1 |
| 2005/0084060 | A1 * | 4/2005 | Seppi | A61B 6/032 378/5 |
| 2006/0115152 | A1 | 6/2006 | Tsuchiya | 382/169 |
| 2007/0036418 | A1 * | 2/2007 | Pan | A61B 6/5288 382/131 |
| 2007/0183667 | A1 * | 8/2007 | Wyatt | G06K 9/4609 382/201 |
| 2008/0051648 | A1 * | 2/2008 | Suri | A61B 6/481 600/407 |
| 2009/0297004 | A1 * | 12/2009 | Baumgart | A61B 6/463 382/130 |
| 2010/0177184 | A1 * | 7/2010 | Berryhill | A61B 5/0059 348/77 |
| 2011/0301980 | A1 * | 12/2011 | Martucci | G06Q 10/06 705/3 |
| 2012/0026317 | A1 | 2/2012 | Nakahira et al. | 348/92 |
| 2012/0063662 | A1 | 3/2012 | Kwon et al. | 382/132 |
| 2012/0121179 | A1 * | 5/2012 | Keshet | G06T 5/002 382/169 |
| 2013/0089247 | A1 * | 4/2013 | Mercuriev | G06T 5/002 382/128 |
| 2013/0261443 | A1 | 10/2013 | Machida | 600/431 |
| 2013/0294674 | A1 | 11/2013 | Miyamoto | 382/132 |
| 2014/0126799 | A1 * | 5/2014 | Miyamoto | G06T 5/003 382/132 |

FOREIGN PATENT DOCUMENTS

| | | |
|---|---|---|
| JP | H04-030786 | 3/1992 |
| JP | H09-248291 | 9/1997 |
| JP | H10-118056 | 5/1998 |
| JP | 2004-321457 | 11/2004 |
| JP | 2011-240178 | 12/2011 |
| JP | 2012-176082 | 9/2012 |

\* cited by examiner

EDGE EMPHASIS IN PROCESSING IMAGES BASED ON RADIATION IMAGES

RELATED APPLICATIONS

This application is a continuation of application Ser. No. 14/058,554, filed Oct. 21, 2013. It claims benefit of that application under 35 U.S.C. § 120, and claims benefit under 35 U.S.C. § 119 of Japanese Patent Application No. 2012-245636, filed Nov. 7, 2012. The entire contents of each of the mentioned prior applications are incorporated herein by reference.

BACKGROUND OF THE INVENTION

Field of the Invention

The present invention relates to emphasis processing for an image obtained by digital subtraction angiography.

Description of the Related Art

With recent advances in the digital technology, it has become popular to perform digital processing for images even in the medical field. Instead of conventional X-ray imaging using an X-ray diagnosis film, two-dimensional X-ray sensors configured to output an X-ray image as a digital image have also prevailed. Digital image processing such as edge emphasis processing for a digital image output from the two-dimensional X-ray sensor is important.

An application example of the digital image processing is DSA processing of acquiring a digital subtraction angiogram (to be referred to as a DSA image hereinafter). The DSA image is an image obtained by acquiring images before and after the inflow of a contrast medium into an object, and subtracting an image (to be referred to as a mask image hereinafter) before the inflow of the contrast medium from an image (to be referred to as a live image hereinafter) after the inflow of the contrast medium. In subtraction processing of the mask image from the live image, a blood vessel region serving as a region of interest in diagnosis is held as a change region between images that is generated by the inflow of the contrast medium. The remaining unnecessary region is removed as a background region, and the change region is expressed as a homogeneous region. The generated DSA image is an image helpful for diagnosis because the blood vessel region can be observed without influencing the remaining object structure.

The purpose of using a DSA image for diagnosis is clear visualization of a contrasted blood vessel image. This purpose is considered to have already been achieved in a subtraction image obtained by subtracting a mask image from a live image. However, an image more suitable for diagnosis is obtained by applying emphasis processing generally used as X-ray image processing to a subtraction image and further emphasizing the edge of a contrasted blood vessel region.

As an example of the emphasis processing, frequency emphasis processing will be explained. More specifically, an image is decomposed into a plurality of band-limited images representing different frequencies. The respective band-limited images undergo different adjustments and then are merged, generating one emphasized image.

As a method of decomposing an image into a plurality of band-limited images, there are various methods such as Laplacian pyramid decomposition, wavelet transform, and unsharp masking. For example, when unsharp masking is adopted, letting Sorg be an original image and Sus be a blurred image, a band-limited image H is given by:

$$H(x,y) = \text{Sorg}(x,y) - \text{Sus}(x,y) \quad (1)$$

where $(x, y)$ is the pixel of an image, and $H(x, y)$, $\text{Sorg}(x, y)$, and $\text{Sus}(x, y)$ are pixel values.

The above equation is used to generate one band-limited image from an original image. A method of generating a plurality of band-limited images representing different frequencies is as follows. A different frequency is represented by a level lv, and a plurality of band-limited images having different frequencies from a high frequency (lv=1) to a low frequency (lv=lvMax) are represented by $\{H_{lv}|lv=1, 2, \ldots, lvMax\}$. At this time, the band-limited image $H_{lv}$ at an arbitrary level lv is given by:

$$H_{lv}(x,y) = (x,y) - \text{Sus}_{lv}(x,y) \quad (2)$$

where $\{\text{Sus}_{lv}|lv=0, 1, 2, \ldots, lvMax\}$ are a plurality of blurred images having different frequencies. A blurred image Sus0 having lv=0 is the original image Sorg.

From equation (2), the relationship between the original image Sorg and the band-limited image $H_{lv}$ is given by:

$$\text{Sorg}(x,y) = \Sigma_{lv}^{lvMax} H_{lv}(x,y) + \text{Sus}_{lvMax}(x,y) \quad (3)$$

This means that the original image Sorg can be reconstructed by adding all the decomposed band-limited images $H_{lv}$ (to be referred to as high-frequency images hereinafter) and a blurred image $\text{Sus}_{lvMax}$ having a lowest frequency (to be referred to as a low-frequency image hereinafter).

Based on this relationship, frequency emphasis processing is given by equation (4) below using a coefficient $\{\alpha_{lv}|lv=1, 2, \ldots, lvMax\}$ which gives an emphasis degree on a high-frequency image:

$$\text{Senh}(x,y) = \Sigma_{lv=1}^{lvMax} \alpha_{lv} H_{lv}(x,y) + \text{Sus}(x,y) \quad (4)$$

where Senh is an image having undergone frequency emphasis processing. When the emphasis coefficient $\alpha_{lv}$ is set to be 1 at all levels, Senh becomes equal to the original image Sorg in accordance with equation (3). A high-frequency image is emphasized by setting the emphasis coefficient $\alpha_{lv}$ to be larger than 1, and suppressed by setting it to be smaller than 1. That is, by setting a different value of the emphasis coefficient $\alpha_{lv}$ for each frequency level lv, the user can create images of his preferences having undergone various frequency emphasis or suppression processes.

However, the emphasis coefficient $\alpha_{lv}$ allows adjustment at each level, but emphasis or suppression is uniformly performed at the same frequency component. That is, this method has a problem that an edge component to be emphasized and a noise component to be suppressed cannot be separated.

To solve this problem, Japanese Patent Laid-Open No. 09-248291 discloses a method of detecting only an edge component from a high-frequency image and emphasizing it, thereby obtaining the emphasis effect of only the edge. Japanese Patent Publication No. 04-030786 discloses a method of performing threshold processing using a predetermined value for each portion of a subtraction image in order to clearly discriminate a blood vessel region in a DSA image from the remaining region, separating only the blood vessel region serving as a region of interest based on the result, and highlighting it.

The following problem arises when the above-described emphasis processing is applied to a DSA image.

The DSA image is a subtraction image obtained by subtracting a mask image from a live image and removing an object structure in order to enhance the contrast of a contrasted region.

In general, a small-pixel-value region in an X-ray image corresponds to a region having a thick object structure. Since the amount of X-rays reaching the sensor is small in the region having the thick object structure, the small-pixel-value region is a region where noise components with a low S/N ratio are dominant Inter-image subtraction removes a clinically unnecessary object structure, but a noise component in such a small-pixel-value region remains on the subtraction image.

For this reason, if emphasis processing is applied to a DSA image, noise in a subtraction image corresponding to the small-pixel-value region before inter-image subtraction is further emphasized by emphasis processing, greatly impairing visibility.

The method disclosed in Japanese Patent Laid-Open No. 09-248291 in which only an edge component is detected and undergoes emphasis processing does not especially target a DSA image, and cannot perform emphasis processing considering noise in a subtraction image. The method disclosed in Japanese Patent Publication No. 04-030786 targets a DSA image, separates only a blood vessel region serving as a region of interest, and highlights it. However, this method does not consider noise dependent on a pixel value before the above-mentioned inter-image subtraction.

SUMMARY OF THE INVENTION

The present invention provides an image processing technique of adaptively performing emphasis processing for a subtraction image in consideration of noise dependent on a pixel value before inter-image subtraction, and generating a high-quality subtraction image.

To achieve the above object, an image processing apparatus according to the present invention comprises the following arrangement. That is, there is provided an image processing apparatus for processing a radiation image, comprising: a subtraction unit configured to generate a subtraction image by performing subtraction between a mask image serving as a radiation image obtained by capturing an object, at least of a specific region of which does not include contrast medium, and a live image serving as a radiation image obtained by capturing the object which includes the contrast medium; a determination unit configured to determine, based on at least one of the mask image and the live image, an emphasis degree serving as a degree of emphasis processing for the subtraction image; and a processing unit configured to perform the emphasis processing for the subtraction image based on the emphasis degree.

According to the present invention, emphasis and suppression can be adaptively performed in consideration of pixel value-dependent noise by using information of a live image before inter-image subtraction in emphasis processing for an image obtained by digital subtraction angiography.

According to the present invention, emphasis and suppression can be adaptively performed relatively quickly in consideration of pixel value-dependent noise by storing and using information of a mask image before inter-image subtraction in emphasis processing for an image obtained by digital subtraction angiography.

Further features of the present invention will become apparent from the following description of exemplary embodiments (with reference to the attached drawings).

DESCRIPTION OF THE EMBODIMENTS

Embodiments of the present invention will now be described in detail with reference to the accompanying drawings.

First Embodiment

An X-ray image processing apparatus serving as a radiation image processing apparatus according to the first embodiment will be explained with reference to FIG. 1.

An X-ray image processing apparatus 100 includes an X-ray generation unit 101 capable of generating X-ray pulses as radiation of 3 to 30 pulses per sec, and a two-dimensional X-ray sensor 104 which receives an X-ray 103 having passed through an object 102 and captures, as an X-ray image (radiation image), a moving image synchronized with X-ray pulses. The two-dimensional X-ray sensor 104 functions as an image capturing unit which captures a moving image of the object 102 irradiated with X-rays.

The X-ray image processing apparatus 100 includes a pre processing unit 105 which performs pre processing for respective frames of a moving image captured by the two-dimensional X-ray sensor 104 at different times.

The X-ray image processing apparatus 100 includes an image storage unit 106 which stores at least one frame of a pre-processed moving image as a mask image before the inflow of contrast medium. A frame to be stored as a mask image is, for example, a frame immediately after the start of moving image capturing, a frame immediately before the inflow of the contrast medium that is automatically acquired upon detecting the inflow of the contrast medium from a moving image, or a frame selected by designating the storage timing by the operator at the start of the inflow of the contrast medium. It is also possible to store a plurality of frames, and appropriately select a frame to be used as a mask image, or merge a plurality of frames.

Further, an image obtained by capturing an object, at least of a specific region which does not include the contrast medium can be used as a mask image. The specific region can be an entire of the image, or a region of interest in a blood vessel region in the image. The region of interest in the blood vessel region can be a partial region with a quarter of size of the image and the same center position of the image.

The X-ray image processing apparatus 100 includes a subtraction unit 107 which subtracts a mask image stored in the image storage unit 106 from a frame (to be referred to as a live image hereinafter) after the inflow of the contrast medium that is output from the pre processing unit 105, and which outputs the resultant image as a subtraction image.

The X-ray image processing apparatus 100 also includes an emphasis degree setting unit 108 which sets an emphasis degree for a subtraction image.

The X-ray image processing apparatus 100 includes an emphasis correction value calculation unit 109 which generates, from a live image output from the pre processing unit 105, an emphasis correction image in which a pixel value represents a correction value for an emphasis degree set by the emphasis degree setting unit 108. The X-ray image processing apparatus 100 includes an emphasis processing unit 110 which performs emphasis processing for a subtraction image based on the emphasis degree and emphasis correction image, generating an emphasis subtraction image. Further, the X-ray image processing apparatus 100 includes an image display unit 111 which displays an emphasis subtraction image output from the emphasis processing unit 110 as a DSA image.

Figure 2:
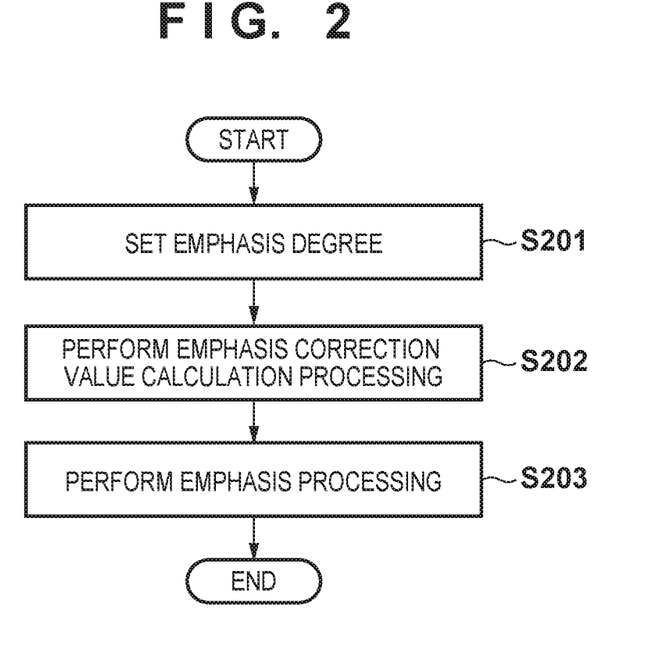
FIG. 2 is a flowchart showing processing according to the first embodiment.

The operations of the emphasis degree setting unit 108, emphasis correction value calculation unit 109, and emphasis processing unit 110 in the first embodiment will be further explained with reference to a flowchart shown in FIG. 2.

In step S201, the emphasis degree setting unit 108 sets an emphasis degree α for a subtraction image based on a user operation. The emphasis degree is generally set while the user confirms a DSA image displayed on the image display unit 111 so as to obtain an emphasis subtraction image of his choice. Note that the emphasis degree may be set to be a different value for each image capturing (imaging). Alternatively, it is also possible to set in advance, in a database (not shown), emphasis degrees for a plurality of types of image capturing conditions such as an X-ray image capturing condition, image capturing portion, and image capturing manipulation, and read out and set an emphasis degree corresponding to an image capturing condition designated at the time of image capturing.

In step S202, the X-ray image processing apparatus 100 inputs a live image output from the pre processing unit 105 to the emphasis correction value calculation unit 109. The emphasis correction value calculation unit 109 outputs an emphasis correction image C from the live image.

For example, the first embodiment will explain a method of generating an emphasis correction image having, as a pixel value, a result of calculating, from a live image for each pixel, an emphasis correction value based on estimation of a noise amount.

Random noise in an X-ray image is represented by $\sigma^2$. The random noise $\sigma^2$ in an X-ray image is theoretically formed from quantum noise $\sigma_Q^2$ proportional to an X-ray amount incident on the two-dimensional X-ray sensor 104, and system noise $\sigma_S^2$ independent of the incident X-ray amount. Here, V is the pixel value of an image that is proportional to the incident X-ray amount, and G is a coefficient for converting the pixel value V into a value equivalent to the incident X-ray amount. Assuming that the quantum noise $\sigma_Q^2$ and system noise $\sigma_S^2$ do not have a correlation, the random noise variance $\sigma^2$ in an X-ray image is given by:

$$\sigma^2(V) = \sigma_Q^2(V/G) + \sigma_S^2 \quad (5)$$

The parameters of the quantum noise $\sigma_Q^2$, system noise $\sigma_S^2$, and gain coefficient G in equation (5) are values uniquely determined in the image capturing process, and can be calculated in advance.

For the pixel (x, y) of a live image, a theoretical noise amount $\sigma^2(V_{x,y})$ corresponding to the average pixel value $V_{x,y}$ of each pixel can be estimated by calculating the average pixel value V from n×n pixels centered on (x, y).

For the pixel (x, y) of a live image, the variance value $\sigma_{x,y}^2$ of arbitrary n×n pixels centered on (x, y) is calculated. If n×n pixels used for calculation do not contain an edge, the variance value $\sigma_{x,y}^2$ takes a value equal to or smaller than the theoretical noise amount $\sigma^2(V_{x,y})$. If n×n pixels used for calculation contain an edge, the variance value $\sigma_{x,y}^2$ becomes larger than the theoretical noise amount $\sigma^2(V_{x,y})$. From this fact, an emphasis correction value C(x, y) of each pixel is given by:

$$C(x, y) = \begin{cases} 1 & \sigma_{x,y}^2 > \sigma^2(V_{x,y}) \\ 0 & \text{(otherwise)} \end{cases} \quad (6)$$

The emphasis correction value C(x, y) is "1" when arbitrary n×n pixels centered on the pixel (x, y) contain an edge, and "0" whey they contain only noise. The emphasis correction image C is generated as a binary image equal in image size to the live image, by calculating emphasis correction values for all the pixels (x, y) of the live image and setting them as the pixel values of the pixels (x, y).

In step S203, the X-ray image processing apparatus 100 inputs the subtraction image, emphasis degree α, and emphasis correction image C to the emphasis processing unit 110 to generate an emphasis subtraction image Senh, and then ends the process. Although various methods are conceivable for the emphasis processing, a case in which unsharp masking already described above is employed will be explained below.

Let Sorg be a subtraction image, $\{H_{lv}|lv=1, 2, \ldots, lvMax\}$ be a high-frequency image generated by frequency decomposition processing, and $Sus_{lvMax}$ be a low-frequency image. Then, the emphasis subtraction image Senh is given by equation (7) below in which the emphasis correction image C is added to equation (4):

$$Senh(x,y) = \Sigma_{lv=1}^{lvMax} \alpha_{lv} \times C(x,y) \times H_{lv}(x,y) + Sus_{lvMax}(x,y) \quad (7)$$

In the above description, the user sets the emphasis degree α for a subtraction image by using the emphasis degree setting unit 108 in step S201. This corresponds to the case of level lv=1 at which only one high-frequency image is generated according to equation (7). When frequency emphasis processing is used as emphasis processing, the level lv is set to be a value lvMax larger than 1, as needed. In this case, the value of the emphasis degree α can be set to a different value for each level lv. Hence, the emphasis degree setting unit 108 is configured to set the emphasis degree to be $\alpha_{lv}$ and allow the user to set the level lv from lv=1 to lv=lvMax. The user may determine a lvMax value, and the frequency decomposition level may be determined in accordance with the lvMax value.

Although equation (7) uses the common emphasis correction image C for all high-frequency images $\{H_{lv}|1 v=1, 2, \ldots, lvMax\}$, the emphasis correction image C may also be calculated for each frequency. In this case, a plurality of blurred images $\{Sus_{lv}|lv=1, 1, 2, \ldots, lvMax\}$ having different frequencies are calculated from a live image. An emphasis correction value is calculated for each level in accordance with equation (6), generating an emphasis correction image $\{C_{lv}|lv=1, 1, 2, \ldots, lvMax\}$. At this time, the emphasis subtraction image Senh is given by:

$$Senh(x,y) = \Sigma_{lv=1}^{lvMax} \alpha_{lv} \times C_{lv}(x,y) \times H_{lv}(x,y) + Sus_{lvMax}(x,y) \quad (8)$$

The emphasis correction value C(x, y) is a binary image in the above description, but may be a multilevel image given by:

$$C(x, y) = \frac{\sigma_{x,y}^2}{\sigma^2(V_{x,y})} \quad (9)$$

In the above equation, when the variance value $\sigma_{x,y}^2$ of arbitrary n×n pixels centered on the pixel (x, y) is larger than the theoretical noise amount $\sigma^2(V_{x,y})$, the emphasis correction value takes a value of 1 or larger. Hence, the value of the pixel (x, y) is emphasized according to equation (7) or (8). To the contrary, when the variance value $\sigma_{x,y}^2$ is smaller than the theoretical noise amount $\sigma^2(V_{x,y})$, the emphasis correction value takes a value smaller than 1. Thus, the value of the pixel (x, y) is suppressed according to equation (7) or (8). That is, the emphasis correction value can be expressed as an edge likelihood index or noise likelihood index without clearly separating an edge and noise.

In the first embodiment, the high-frequency image H is generated from a subtraction image. Therefore, the high-frequency image H contains blood vessel edge information serving as a clinical region of interest, but a clinically unnecessary object structure is removed by inter-image subtraction. However, radiation dose-dependent noise in a region where a thick object structure is captured remains. That is, the high-frequency image H is an image representing, by large pixel values, a blood vessel edge serving as a clinical region of interest and noise in a low-radiation-dose region.

In contrast, the emphasis correction image C is generated from a live image. In the emphasis correction image C, edge information and noise are separated by estimating the amount of radiation dose-dependent noise. However, the emphasis correction image C contains the edge of an unnecessary object structure which should be removed by inter-image subtraction. That is, in the emphasis correction image C, the edge region is represented by 1 (or a value of 1 or larger), and the remaining region is represented by 0 (or a value smaller than 1) regardless of whether the target region is a clinical region of interest.

According to equation (7) or (8), a blood vessel edge serving as a clinical region of interest contained in the high-frequency image H is also an edge in the emphasis correction image C, and the pixel value is saved or emphasized because it is multiplied by a value of 1 or larger. Noise contained in the high-frequency image H is noise other than an edge in the emphasis correction image C, and the pixel value is suppressed or set to be 0 because it is multiplied by a value smaller than 1. Further, the edge of a clinically unnecessary region contained in the emphasis correction image C has a small value in the high-frequency image H and is suppressed by multiplication. Adjustment (frequency emphasis or frequency suppression) is performed for each band-limited image by multiplying the emphasis degree $\alpha_{lv}$ of each frequency.

As described above, according to the first embodiment, when performing emphasis processing for a subtraction image at an emphasis degree set by the user, an emphasis correction value considering radiation dose-dependent noise is calculated from a live image and used. Hence, emphasis processing can be adaptively performed for a subtraction image.

Second Embodiment

An X-ray image processing apparatus according to the second embodiment will be explained with reference to FIG. 3.

Similar to the first embodiment, an X-ray image processing apparatus 300 includes an X-ray generation unit 101, two-dimensional X-ray sensor 104, pre processing unit 105, image storage unit 106, subtraction unit 107, and image display unit 111. Also, the X-ray image processing apparatus 300 includes an emphasis degree setting unit 108 which sets an emphasis degree for a subtraction image, and an emphasis correction value calculation unit 109 which generates an emphasis correction image representing a correction value (correction coefficient) for the emphasis degree. These units are the same as those in the first embodiment, and a description thereof will not be repeated.

The X-ray image processing apparatus 300 includes an edge detection unit 301 which detects an edge from a subtraction image output from the pre processing unit 105, generating an edge image in which a pixel value expresses edge information. The X-ray image processing apparatus 300 further includes an emphasis processing unit 302 which performs emphasis processing for a subtraction image based on the edge image in addition to the emphasis degree and emphasis correction image, generating an emphasis subtraction image.

Figure 4:
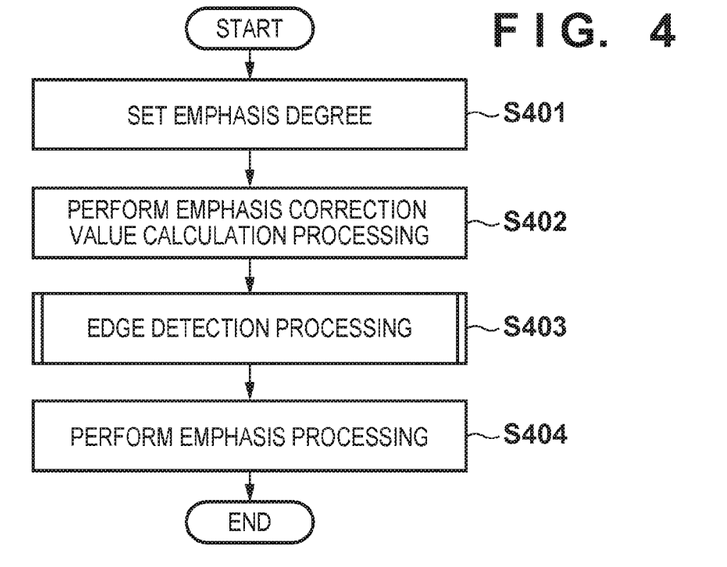
FIG. 4 is a flowchart showing processing according to the second embodiment.

The operations of the emphasis degree setting unit 108, edge detection unit 301, emphasis correction value calculation unit 109, and emphasis processing unit 302 in the second embodiment will be further explained with reference to a flowchart shown in FIG. 4. Note that some processes overlap the contents described with reference to the flowchart of FIG. 2 in the first embodiment, and the operation will be described in detail based on only a different flowchart.

In step S401, the emphasis degree setting unit 108 sets the emphasis degree α for a subtraction image based on a user operation. As described in the first embodiment, when frequency emphasis processing is used as emphasis processing, $\alpha_{lv}$ corresponding to a plurality of frequencies from lv=1 to lv=lvMax may be set.

In step S402, the X-ray image processing apparatus 300 inputs a live image output from the pre processing unit 105 to the emphasis correction value calculation unit 109. The emphasis correction value calculation unit 109 outputs an emphasis correction image C from the live image.

In step S403, the X-ray image processing apparatus 300 inputs a subtraction image to the edge detection unit 301, generating an edge image E.

In step S404, the X-ray image processing apparatus 300 inputs the subtraction image, edge image E, emphasis degree α, and emphasis correction image C to the emphasis processing unit 302 to generate an emphasis subtraction image Senh, and then ends the process. The emphasis subtraction image Senh is given by equation (10) below in which the edge image E is added to equation (7) or (8):

$$Senh(x, y) = \sum_{lv=1}^{lvMax} \alpha_{lv} \times C_{lv}(x, y) \times E_{lv}(x, y) \times H_{lv}(x, y) + Sus_{lvMax}(x, y) \quad (10)$$

where the suffix lv of α, C, E, and H is the frequency, similar to the description of the first embodiment. Especially, as for C and E, lv may be set to be 1 to obtain one image.

Alternatively, a plurality of blurred images having different frequencies may be obtained from a live image and subtraction image, and the emphasis correction value or edge may be detected from these images.

Various methods are applicable to generation of the edge image E in step S403. For example, the operation of the edge detection unit 301 when the Canny edge detection method is used will be explained with reference to a flowchart shown in FIG. 5.

Figure 5:
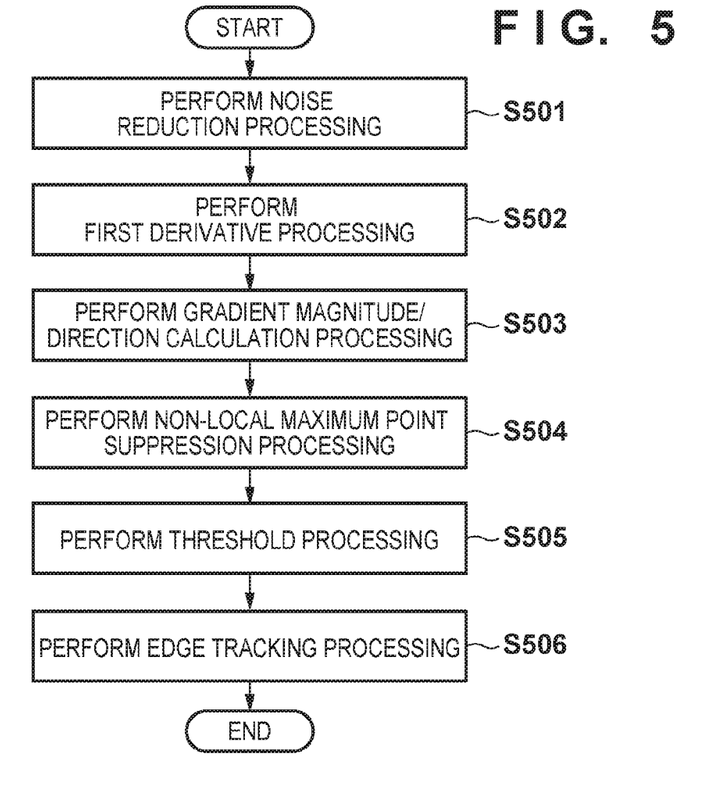
FIG. 5 is a flowchart showing in detail edge detection processing according to the second embodiment.

In step S501, the edge detection unit 301 performs noise reduction processing using a Gaussian filter for an input subtraction image, generating a noise reduction image N.

In step S502, the edge detection unit 301 performs first derivative processing for the noise reduction image N in the horizontal and vertical directions, generating a horizontally differentiated image DX and vertically differentiated image DY. In the first derivative processing, for example, an edge detection operator such as a Roberts, Prewitte, or Sobel operator is used. The horizontally differentiated image DX and vertically differentiated image DY are images in which the value of each pixel has information about the magnitude and direction of a gradient in the horizontal or vertical direction.

In step S503, the edge detection unit 301 calculates a gradient magnitude image MAG and gradient direction image THETA from the horizontally differentiated image DX and vertically differentiated image DY in accordance with:

$$MAG = \sqrt{DX^2 + DY^2} \qquad (11)$$

$$THETA = \arctan\left(\frac{DY}{DX}\right) \qquad (12)$$

The gradient magnitude image MAG is an image in which the value of each pixel represents the magnitude of a gradient. The gradient direction image THETA is an image in which a pixel whose pixel value increases in the horizontal direction is represented by 0, a pixel whose pixel value increases in the vertical direction is represented by $\Pi/2$, and the value of each pixel represents the direction of a gradient by using a value of $-\Pi/2$ (inclusive) to $\Pi/2$ (exclusive).

In step S504, the edge detection unit 301 performs non-local maximum point suppression processing based on the gradient magnitude image MAG and gradient direction image THETA, and outputs an edge candidate image E as edge information. The edge candidate image E is a binary image obtained by representing local maximum edge pixels by 1 and the remaining pixels by 0 in a noise reduction image. In the non-local maximum point suppression processing, two pixels adjacent to a pixel (x, y) of interest are selected based on the gradient direction image THETA(x, y). When the gradient magnitude image MAG(x, y) of the pixel (x, y) of interest is larger than the values of the two adjacent pixels, the pixel (x, y) of interest is regarded as a local maximum edge pixel, and E(x, y)=1 is set. An example of this processing is as follows.

When the gradient direction image THETA(x, y) is $-\Pi/8$ (inclusive) to $\Pi/8$ (exclusive), two pixels in the horizontal direction are set as adjacent pixels, and E(x, y) is calculated according to:

$$E(x, y) = \begin{cases} 1 & (MAG(x-1, y) < MAG(x, y)) \text{ and} \\ & MAG(x, y) > MAG(x+1, y)) \\ 0 & (\text{otherwise}) \end{cases} \qquad (13)$$

When the gradient direction image THETA(x, y) is $\Pi/8$ (inclusive) to $3\Pi/8$ (exclusive), two pixels in the oblique direction are set as adjacent pixels, and E(x, y) is calculated according to:

$$E(x, y) = \begin{cases} 1 & (MAG(x, y) > MAG(x-1, y-1)) \text{ and} \\ & MAG(x, y) > MAG(x+1, y+1)) \\ 0 & (\text{otherwise}) \end{cases} \qquad (14)$$

When the gradient direction image THETA(x, y) is $3\Pi/8$ (inclusive) to $\Pi/2$ (exclusive) or $-\Pi/2$ (inclusive) to $-3\Pi/8$ (exclusive), two pixels in the vertical direction are set as adjacent pixels, and E(x, y) is calculated according to:

$$E(x, y) = \begin{cases} 1 & (MAG(x, y) > MAG(x, y-1)) \text{ and} \\ & MAG(x, y) > MAG(x, y+1)) \\ 0 & (\text{otherwise}) \end{cases} \qquad (15)$$

When the gradient direction image THETA(x, y) is $-3\Pi/8$ (inclusive) to $-\Pi/8$ (exclusive), two pixels in the oblique direction are set as adjacent pixels, and E(x, y) is calculated according to:

$$E(x, y) = \begin{cases} 1 & (MAG(x, y) > MAG(x-1, y+1)) \text{ and} \\ & MAG(x, y) > MAG(x+1, y-1)) \\ 0 & (\text{otherwise}) \end{cases} \qquad (16)$$

In step S505, the edge detection unit 301 performs threshold processing for the edge candidate image E based on the gradient magnitude image MAG and two thresholds Tlow and Thigh (Tlow<Thigh), and outputs a weak edge image Elow and strong edge image Ehigh. The weak edge image Elow is a binary image obtained by comparing the gradient magnitude image MAG(x, y) and the Tlow value for all pixels (x, y) serving as the edge candidate image E(x, y)=1, and setting the values of pixels having MAG(x, y)>Tlow to be 1 and those of the remaining pixels to be 0. The strong edge image Ehigh is a binary image obtained by comparing the gradient magnitude image MAG(x, y) and Thigh for all pixels (x, y) serving as the edge candidate image E(x, y)=1, and setting the values of pixels having MAG(x, y)>Thigh to be 1 and those of the remaining pixels to be 0.

In step S506, the edge detection unit 301 performs edge tracking processing based on the weak edge image Elow and strong edge image Ehigh, and outputs an edge image HE. In the edge tracking processing, when the concatenation component of the pixels (x, y) serving as the weak edge image Elow(x, y)=1 contains a pixel (x, y) in the strong edge image Ehigh(x, y)=1, all the pixels (x, y) forming the concatenation component are regarded as edge pixels, and E(x, y)=1 is set. The remaining pixels (x, y) are non-edge pixels, and E(x, y)=0 is set. The edge image E acquired by the above processing is output as a result E of the Canny edge detection method for the subtraction image. After that, the Canny edge detection processing ends.

Note that this edge detection processing may be applied to the high-frequency image $H_{lv}$ generated from a subtraction image. In this case, edge detection is performed for respective high-frequency images $H_{lv}$ having lv=0 to lv=lvMax, and the result is output as $E_{lv}$.

The edge detection target in the second embodiment is the edge of a contrasted blood vessel region serving as clinically helpful image information. The characteristic of the edge varies depending on the state of the inflow of the contrast medium.

In the above-described edge detection processing, the operator used in the noise reduction processing or first derivative processing may be adaptively switched in accordance with the time after the start of the inflow of the contrast medium. When the frame rate in image capturing is high, part of the noise reduction processing, threshold processing, and edge tracking processing may be omitted or replaced with relatively simple processing in order to increase the processing speed. Another example of the edge detection processing is a zero crossing method of detecting a zero crossing based on second derivative processing.

As described above, according to the second embodiment, the edge image E is generated from a subtraction image. The edge image E is an image obtained by extracting an edge using information such as the edge intensity, direction, or continuity which is not considered in only the subtraction image. By adding this image to the equation of frequency emphasis processing, the second embodiment can implement adaptive edge emphasis and noise suppression at higher precision.

Third Embodiment

An X-ray image processing apparatus according to the third embodiment will be explained with reference to FIG. 6.

Similar to the first and second embodiments, an X-ray image processing apparatus 600 includes an X-ray generation unit 101, two-dimensional X-ray sensor 104, pre processing unit 105, image storage unit 106, subtraction unit 107, and image display unit 111. Also, the X-ray image processing apparatus 600 includes an emphasis degree setting unit 108 which sets an emphasis degree for a subtraction image. These units are the same as those in the first and second embodiments, and a description thereof will not be repeated.

The X-ray image processing apparatus 600 includes an emphasis correction value calculation unit 601 which generates, from a mask image stored in the image storage unit 106, an emphasis correction image in which a pixel value represents a correction value (correction coefficient) for an emphasis degree set by the emphasis degree setting unit 108.

The X-ray image processing apparatus 600 includes an emphasis correction value storage unit 602 which stores an emphasis correction image of at least one frame output from the emphasis correction value calculation unit 601. Also, the X-ray image processing apparatus 600 includes an emphasis processing unit 603 which performs emphasis processing for a subtraction image based on the emphasis degree and the emphasis correction image stored in the emphasis correction value storage unit 602, generating an emphasis subtraction image.

Figure 7:
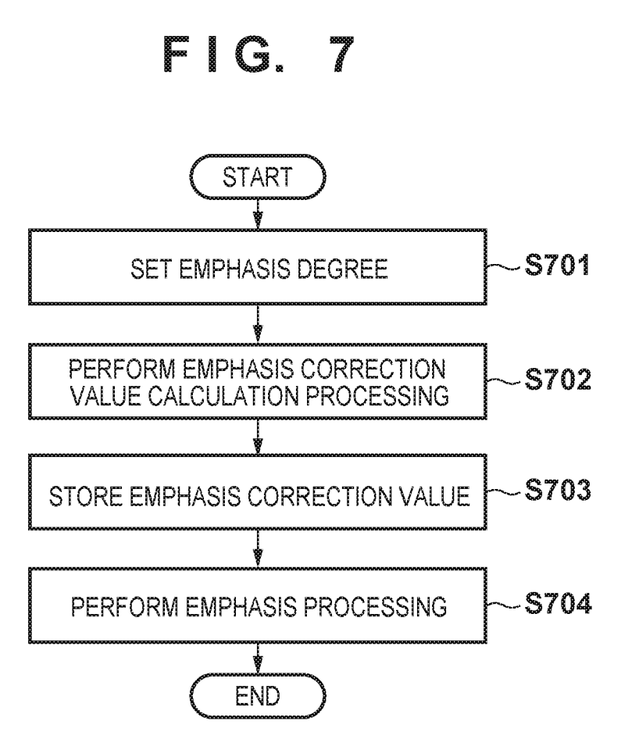
FIG. 7 is a flowchart showing processing according to the third embodiment.

The operations of the emphasis degree setting unit 108, emphasis correction value calculation unit 601, emphasis correction value storage unit 602, and emphasis processing unit 603 in the third embodiment will be further explained with reference to a flowchart shown in FIG. 7. Note that some processes overlap the contents described with reference to the flowchart of FIG. 2 in the first embodiment and the flowchart of FIG. 4 in the second embodiment, and the operation will be described in detail based on only a different flowchart.

In step S701, the user sets the emphasis degree α for a subtraction image by using the emphasis degree setting unit 108. As described in the first embodiment, when frequency emphasis processing is used as emphasis processing, $\alpha_{lv}$ corresponding to a plurality of frequencies from lv=1 to lv=lvMax may be set.

In step S702, the X-ray image processing apparatus 600 inputs a mask image output from the image storage unit 106 to the emphasis correction value calculation unit 601. The emphasis correction value calculation unit 601 outputs an emphasis correction image C from the mask image.

In step S703, the X-ray image processing apparatus 600 stores, in the emphasis correction value storage unit 602, the emphasis correction image C output from the emphasis correction value calculation unit 601.

In step S704, the X-ray image processing apparatus 600 inputs the subtraction image, emphasis degree α, and emphasis correction image C to the emphasis processing unit 603 to generate an emphasis subtraction image Senh, and then ends the process. Here, the emphasis correction image C stored in the emphasis correction value storage unit 602 is read out and used. The emphasis subtraction image Senh is given by the same equation as equation (7) or (8).

In step S702, unlike the first and second embodiments, the emphasis correction value calculation unit 601 receives a mask image and generates the emphasis correction image C in accordance with, for example:

$$C(x,y)=kV_{x,y} \tag{17}$$

In the above equation, a value obtained by multiplying the average value of arbitrary n×n pixels centered on the pixel (x, y) by a predetermined coefficient k is used as the emphasis correction value C(x, y) in the pixel (x, y). By using the emphasis correction image C, the emphasis subtraction image Senh calculated according to equation (7) can be emphasized or suppressed in proportion to the pixel value of the mask image.

In general, a region where the pixel value is small (that is, the incident X-ray amount is small) in an X-ray image is a region where a large amount of noise exists and the S/N ratio is low. Considering this, the coefficient k is set so that C<1 in a small-pixel-value region having a low S/N ratio in the mask image. This setting produces the suppression effect on the subtraction image.

Unlike the first and second embodiments, the third embodiment uses a mask image to calculate an emphasis correction value. Since the mask image is an image before the inflow of contrast medium, unlike a live image, it is impossible to extract the edge of a blood vessel region and set it as an emphasis correction value. Generally in creation of a DSA image, a mask image is created once, saved in the image storage unit, and is not updated after that. As long as the emphasis correction image C generated from the mask image is saved in the emphasis correction value storage unit 602, the saved emphasis correction image C can be read out and used in subsequent processing.

As described above, according to the third embodiment, an emphasis subtraction image can be generated more quickly than by the arrangements described in the first and second embodiments. The third embodiment is effective particularly in an image processing apparatus requiring a high frame rate.

(Information Processing Apparatus)

Figure 1:
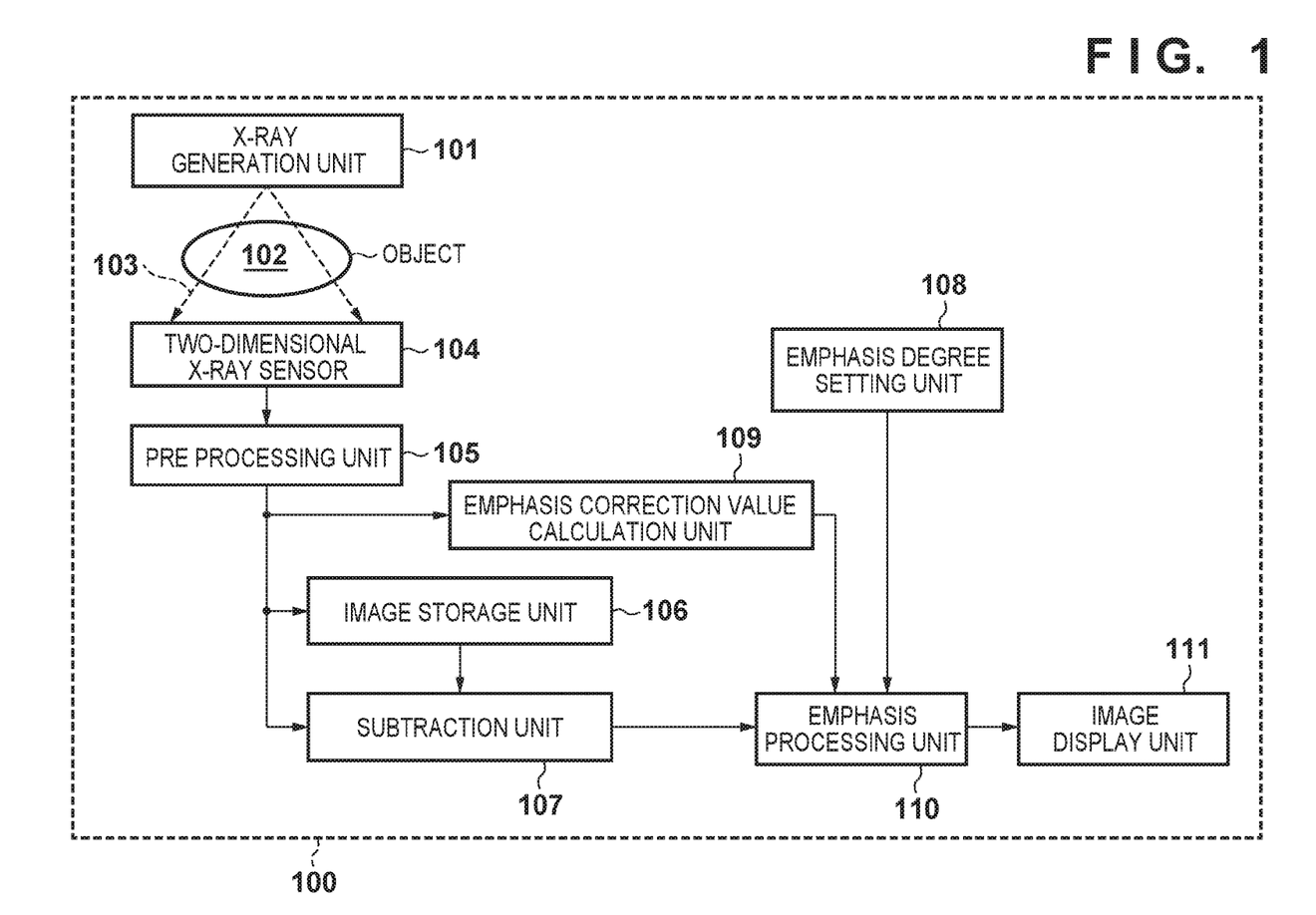
FIG. 1 is a block diagram for explaining the arrangement of an X-ray image processing apparatus according to the first embodiment.
Figure 3:
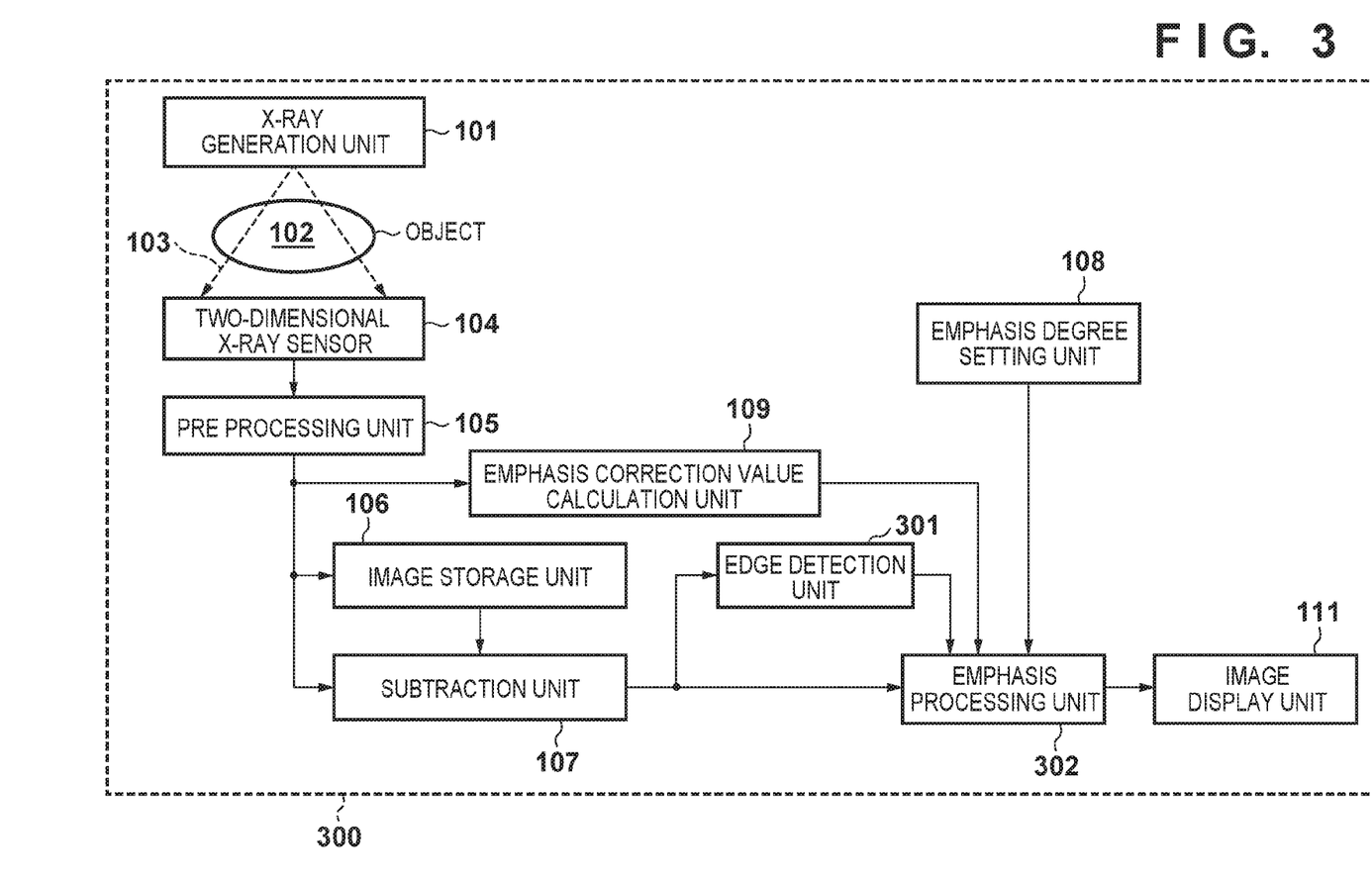
FIG. 3 is a block diagram for explaining the arrangement of an X-ray image processing apparatus according to the second embodiment.
Figure 6:
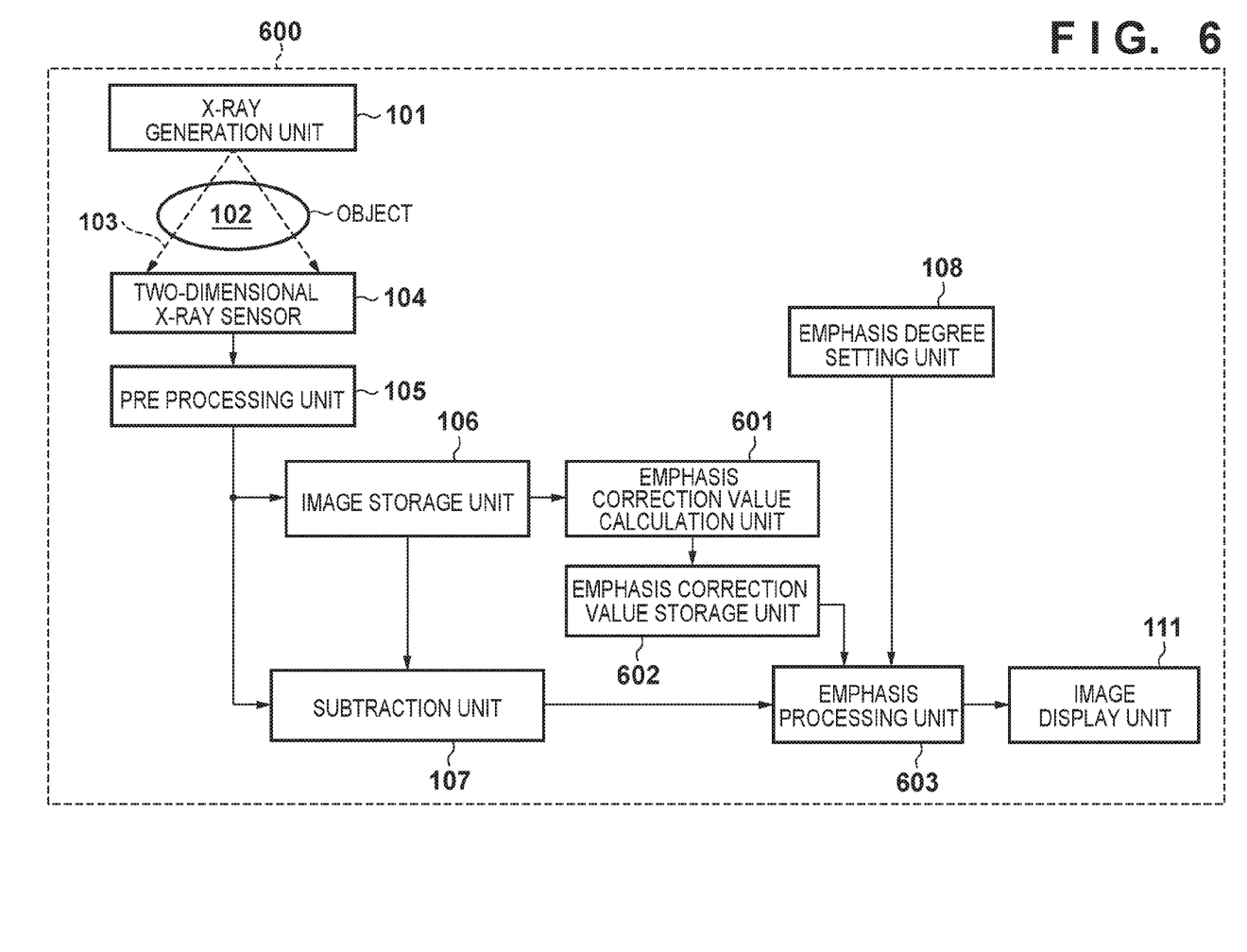
FIG. 6 is a block diagram for explaining the arrangement of an X-ray image processing apparatus according to the third embodiment.

The respective building components shown in FIGS. 1, 3, and 6 may be formed from dedicated hardware, but the functional arrangement of hardware may be implemented by software. In this case, the functions of the respective building components shown in FIGS. 1, 3, and 6 can be implemented by installing software in the information processing apparatus, and executing the software to implement the image processing method by using the calculation function of the information processing apparatus. By executing the software, for example, pre processing is performed for each frame of a moving image output from the two-dimensional X-ray sensor 104 to acquire a mask image and live image before and after the inflow of contrast medium, and a subtraction image is acquired by inter-image subtraction. Then, frequency decomposition processing for the subtraction image, edge detection processing, emphasis correction value calculation processing using a mask image or live image, and an emphasis processing step using the result are executed.

Figure 8:
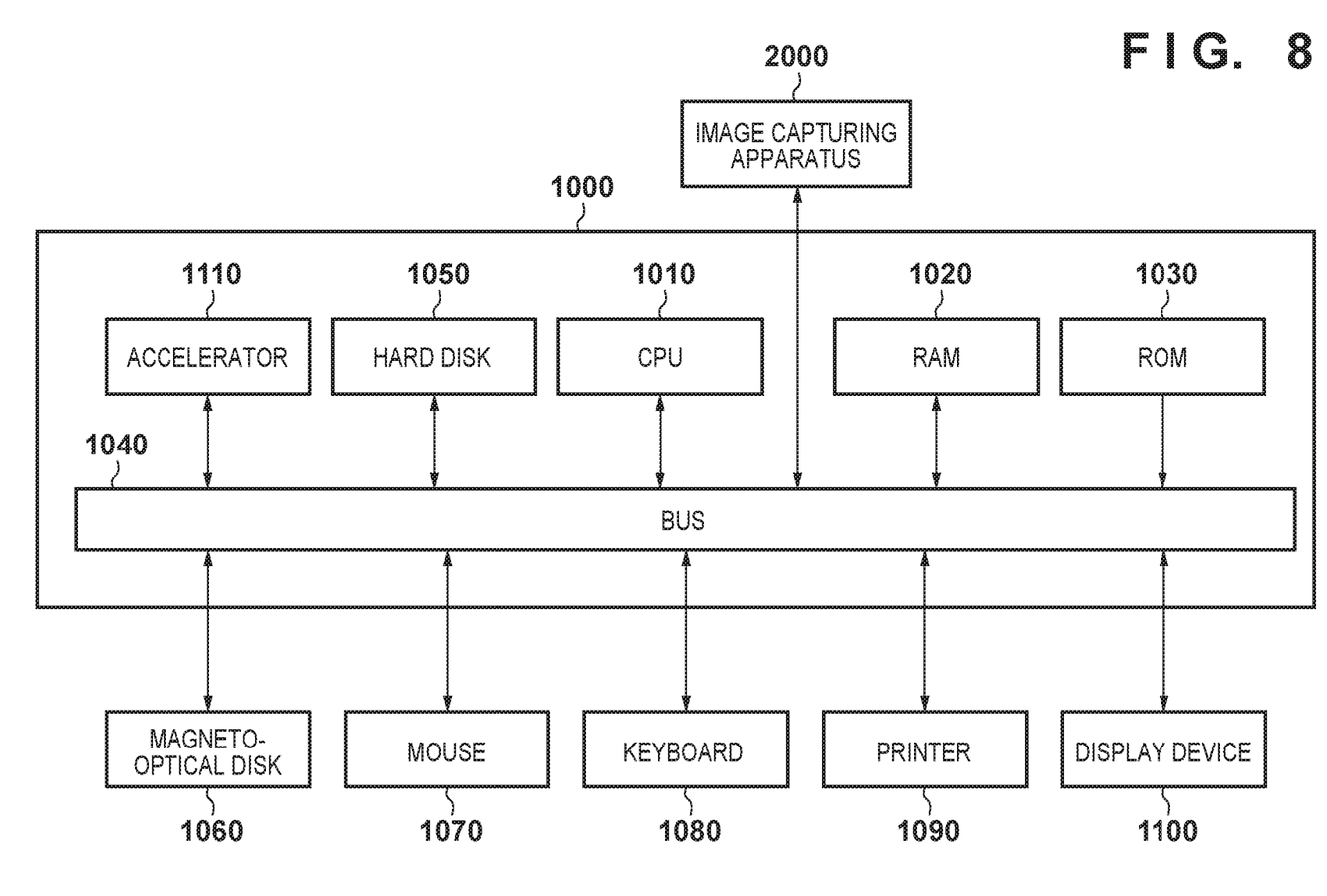
FIG. 8 is a block diagram exemplifying a computer system capable of implementing the present invention.

FIG. 8 is a block diagram showing the hardware arrangement of the information processing apparatus and the arrangement of its peripheral devices. An information processing apparatus 1000 is connected to an image capturing apparatus 2000, and can communicate data with it.

A CPU 1010 can control the overall information processing apparatus 1000 by using programs and data stored in a RAM 1020 and ROM 1030, and execute calculation processing regarding predetermined image processing by executing programs.

The RAM 1020 has an area for temporarily storing programs and data loaded from a magneto-optical disk 1060 and hard disk 1050. Further, the RAM 1020 has an area for temporarily storing image data such as a mask image, live image, and subtraction image acquired from the image capturing apparatus 2000. The RAM 1020 also has a work area to be used when the CPU 1010 executes various processes. The ROM 1030 stores the setting data and boot program of the information processing apparatus 1000 and the like.

The hard disk 1050 holds an OS (Operating System), and programs and data which cause the CPU 1010 of the computer to execute processes to be performed by the respective building components shown in FIGS. 1, 3, and 6. These programs and data are loaded into the RAM 1020 under the control of the CPU 1010, as needed, and processed by the CPU 1010 (computer). Data of a mask image, live image, and subtraction image can also be saved in the hard disk 1050.

The magneto-optical disk 1060 is an example of an information storage medium. Some or all programs or data saved in the hard disk 1050 can be stored in the magneto-optical disk 1060.

A mouse 1070 and keyboard 1080 can be operated by the operator of the information processing apparatus 1000 to input, to the CPU 1010, various instructions such as the setting of the emphasis degree for each frequency by the emphasis degree setting unit 108.

A printer 1090 can print out, on a printing medium, an image displayed on the image display unit 111. An accelerator 1110 can improve a predetermined function or processing performance of the respective building components in the information processing apparatus 1000.

A display device 1100 is formed from a CRT, liquid crystal screen, or the like, and can display the result of processing by the CPU 1010 as an image, character, or the like. For example, the display device 1100 can display an image which is processed by the respective building components shown in FIGS. 1 and 2 and is finally output from the image display unit 111. In this case, the image display unit 111 functions as a display control unit for displaying an image on the display device 1100. A bus 1040 connects the respective building components in the information processing apparatus 1000, and can transmit/receive data between them.

(Image Capturing Apparatus 2000)

Next, the image capturing apparatus 2000 will be explained. The image capturing apparatus 2000 can capture a moving image during the inflow of contrast medium, like an X-ray fluoroscopic apparatus. The image capturing apparatus 2000 transmits the captured image data to the information processing apparatus 1000. Note that a plurality of image data may be transmitted at once to the information processing apparatus 1000, or image data may be transmitted sequentially every time an image is captured.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing method comprising:
generating a subtraction image obtained by performing subtraction processing between a mask radiation image before an inflow of contrast medium and a live radiation image after the inflow of contrast medium;
setting an emphasis degree for enhancing of the subtraction image;
determining, for each pixel included in the subtraction image, existence or absence of an edge in the live radiation image based on a pixel value of a pixel of the live radiation image at a position corresponding to a position of the pixel in the subtraction image, and determining a correction coefficient to correct the emphasis degree in accordance with the existence or absence of the edge; and
enhancing pixel value for each of a plurality of pixels included in the subtraction image based on the emphasis degree and the correction coefficient.

2. The image processing method according to claim 1, wherein in the determining, the correction coefficient for each of the plurality of pixels included in the subtraction image is determined based on (i) a pixel value of a pixel of the live radiation image and (ii) information of at least one of an image capturing condition, an image capturing portion, and an image capturing manipulation, of any one of the mask radiation image and the live radiation image.

3. The image processing method according to claim 1, wherein in the determining, the correction coefficient is determined based on (i) a predetermined first value, and (ii) a second value determined for each of the plurality of pixels included in the subtraction image based on a pixel value of a pixel of the mask radiation image.

4. The image processing method according to claim 3, wherein in the determining, the first value is determined based on an operation input by a user and information of at least one of an image capturing condition, an image capturing portion, and an image capturing manipulation, of any one of the mask radiation image and the live radiation image.

5. The image processing method according to claim 1, wherein in the determining, the correction coefficient is determined based on (i) a first value set by an operation input of a user, and (ii) a second value determined for each of the plurality of pixels included in the subtraction image based on a pixel value of a pixel of the mask radiation image.

6. The image processing method according to claim 1, wherein in the determining, the correction coefficient is determined based on, for each of the plurality of pixels included in the subtraction image, (i) a first value representing a noise determined by a value of the pixel, and (ii) a second value representing a dispersion of pixels of a partial region including the pixel, the correction coefficient being for the pixel.

7. The image processing method according to claim 6, wherein the determining includes calculating the first value based on a relationship equation between a value of the pixel and a dispersion value of a noise, and calculating, as the second value, a dispersion value of pixel values of a partial region including the pixel.

8. The image processing method according to claim 1, further comprising:
applying frequency decomposition processing to the subtraction image,
wherein in the obtaining, an enhanced image of the subtraction image is obtained by multiplying (i) pixel values obtained by the frequency decomposition processing by (ii) correction coefficients respectively determined for pixel values of the subtraction image corresponding to the pixel values.

9. The image processing method according to claim 8, wherein in the determining, a first value is determined for each frequency component obtained by applying frequency decomposition processing to the subtraction image, and
the correction coefficient is determined based on (i) the first value, and (ii) a second value determined for each of the plurality of pixels included in the subtraction image based on a pixel value of a pixel of the mask radiation image.

10. The image processing method according to claim 1, further comprising:
applying edge detection processing to the subtraction image,
wherein in the determining, the correction coefficient is determined based on (i) a predetermined first value, (ii) a second value determined for each of the plurality of pixels included in the subtraction image based on a pixel value of a pixel of the mask radiation image, and (iii) a detection result by edge detection processing to the subtraction image.

11. The image processing method according to claim 10, wherein the applying edge detection processing to the subtraction image is performed based on an intensity of a spatial gradient of neighboring pixel values of the subtraction image, a direction of the spatial gradient, and a continuity of the spatial gradient.

12. The image processing method according to claim 1, further comprising:
determining image processing to be applied to the subtraction image based on information representing an inflow state of the contrast medium of the object to be examined;
applying the determined image processing to the subtraction image; and
determining the correction coefficient for each of the plurality of pixels included in the subtraction image, based on (i) a pixel value of a pixel of the mask radiation image, and (ii) an applied result of the determined image processing.

13. An image processing apparatus comprising:
a processor; and
a memory storing a program that causes the processor to:
generate a subtraction image obtained by performing subtraction processing between a mask radiation image before an inflow of contrast medium and a live radiation image after the inflow of contrast medium;
set an emphasis degree for enhancing of the subtraction image;
determine, for each pixel included in the subtraction image, an existence or absence of an edge in the live radiation image based on a pixel value of a pixel of the live radiation image at a position corresponding to a position of the pixel in the subtraction image, and determine a correction coefficient to correct the emphasis degree in accordance with the existence or absence of the edge; and
enhance pixel value for each of a plurality of pixels included in the subtraction image based on the emphasis degree and the correction coefficient.

14. A non-transitory computer-readable storage medium storing a computer program for causing a computer to execute an image processing method comprising:
generating a subtraction image obtained by performing subtraction processing between a mask radiation image before an inflow of contrast medium and a live radiation image after the inflow of contrast medium;
setting an emphasis degree for enhancing of the subtraction image;
determining, for each pixel included in the subtraction image, an existence or absence of an edge in the live radiation image based on a pixel value of a pixel of the live radiation image at a position corresponding to, a position of the pixel in the subtraction image, and determining a correction coefficient to correct the emphasis degree in accordance with the existence or absence of the edge; and
enhancing pixel value for each of a plurality of pixels included in the subtraction image based on the emphasis degree and the correction coefficient.

15. The image processing method according to claim 1, further comprising:
extracting the edge by comparing a variance value of pixels with a noise amount corresponding to a pixel value.

16. The image processing method according to claim 1, further comprising:
extracting the edge by comparing 1) a variance value of each pixel and peripheral pixels thereof with 2) a theoretical noise amount corresponding to an average pixel value of the pixel and the peripheral pixels.

* * * * *